United States Patent
Senetar

(10) Patent No.: US 10,647,623 B2
(45) Date of Patent: May 12, 2020

(54) PROCESSES FOR REDUCED OXYGENATED RECYCLE IN AN MTO CONVERSION

(71) Applicant: UOP LLC, Des Plaines, IL (US)

(72) Inventor: John J. Senetar, Naperville, IL (US)

(*) Notice: Subject to any disclaimer, the term of this patent is extended or adjusted under 35 U.S.C. 154(b) by 0 days.

(21) Appl. No.: 16/100,564

(22) Filed: Aug. 10, 2018

(65) Prior Publication Data
US 2020/0048160 A1    Feb. 13, 2020

(51) Int. Cl.
*C07C 1/20* (2006.01)
*B01J 19/24* (2006.01)

(52) U.S. Cl.
CPC ............ *C07C 1/20* (2013.01); *B01J 19/24* (2013.01); *B01J 2219/24* (2013.01)

(58) Field of Classification Search
None
See application file for complete search history.

(56) References Cited

U.S. PATENT DOCUMENTS

| | | | |
|---|---|---|---|
| 5,817,906 A | 10/1998 | Marker et al. | |
| 6,166,282 A | 12/2000 | Miller | |
| 6,403,854 B1 | 11/2002 | Miller et al. | |
| 7,132,580 B1 | 7/2006 | Senetar | |
| 7,138,557 B2 | 11/2006 | Senetar | |
| 7,309,679 B2 | 12/2007 | Karch et al. | |
| 7,423,191 B2 | 9/2008 | Senetar et al. | |
| 7,919,660 B2 | 4/2011 | Vora et al. | |
| 9,452,957 B2 | 9/2016 | Senetar et al. | |
| 9,643,897 B2 | 5/2017 | Jan et al. | |
| 2009/0005624 A1 | 1/2009 | Bozzano | |
| 2015/0376080 A1* | 12/2015 | Rothaemel | C10G 11/02 585/254 |
| 2016/0068452 A1* | 3/2016 | Rothamel | B01J 19/24 585/324 |
| 2016/0145169 A1* | 5/2016 | Rothaemel | C10G 3/42 585/254 |
| 2017/0362141 A1* | 12/2017 | Castillo-Welter | B01J 8/0492 |
| 2018/0002610 A1* | 1/2018 | Joensen | C07C 29/141 |
| 2018/0305626 A1* | 10/2018 | Bauer | C07C 41/09 |

FOREIGN PATENT DOCUMENTS

WO    2013186072 A1    12/2013

OTHER PUBLICATIONS

Azizi, Zoha, et al., Dimethyl ether: A Review of Technologies and Production Challenges, Chemical Engineering and Processing: Process Intensification, vol. 82, Aug. 2014, pp. 150-172. (Abstract Only).
International Search Report and Written Opinion for PCT/US2019/046153 corresponding to present application, dated Nov. 21, 2019.

* cited by examiner

*Primary Examiner* — Ali Z Fadhel

(57) ABSTRACT

Processes and an apparatus for reducing heavy oxygenate recycle for an MTO reaction zone. After separating product and water from the MTO reaction effluent, an oxygenate rich stream is passed to a conversion zone in which methanol in the oxygenate rich stream is converted into DME. A DME rich stream is separated from heavy oxygenates and is recycled back to the MTO reaction zone. The conversion zone may include a reactive distillation column, or the conversion zone may include a reactor vessel and a separate separation vessel.

20 Claims, 2 Drawing Sheets

PROCESSES FOR REDUCED OXYGENATED RECYCLE IN AN MTO CONVERSION

FIELD OF THE INVENTION

This invention relates generally to processes for converting methanol to olefins, and more particularly to processes which reduce the byproducts recycled to the methanol-to-olefin reactor.

BACKGROUND OF THE INVENTION

The use of plastics and rubbers are widespread. The production of these plastics and rubbers are from the polymerization of monomers which are generally produced from petroleum. The monomers are generated by the breakdown of larger molecules to smaller molecules which can be modified. The monomers are then reacted to generate larger molecules comprising chains of the monomers. An important example of these monomers is light olefins, including ethylene and propylene, which represent a large portion of the worldwide demand in the petrochemical industry. Light olefins, and other monomers, are used in the production of numerous chemical products via polymerization, oligomerization, alkylation and other well-known chemical reactions. Producing large quantities of light olefin material in an economical manner, therefore, is a focus in the petrochemical industry. These monomers are essential building blocks for the modern petrochemical and chemical industries. The main source for these materials in present day refining is the steam cracking of petroleum feeds.

With the increase in demand, other sources for monomers are providing for an increase in supply while becoming economical. Sources include natural gas and coal conversion, wherein the natural gas and coal are converted to oxygenates and subsequently the oxygenates are converted to light olefins. The product stream from an oxygenates to olefins conversion process needs to be purified to recover the light olefins. Due to the different chemistry from the conversion of petroleum feedstocks to light olefins, the separation and clean-up of the process stream from the oxygenates to olefins conversion process is therefore different.

The production of light olefins (e.g., ethylene and propylene) from oxygenates, and in particular methanol, also generates various oxygenate byproducts. While some of these byproducts can be recovered and recycled to the conversion reactor, some of the byproducts are can foul and plug downstream equipment and may also lead to separation issues (e.g., emulsions, foaming, oil entrainment).

In a commercial methanol to olefins (MTO) design, oxygenates are recycled to the MTO reactor, which results in a build-up of concentration of oxygenates in the reactor recycle. As used hereinafter, the common term methanol to olefins, or MTO, is meant to refer to any oxygenate to olefins conversion process that can be covered by this disclosure. While it is desirable to recycle dimethylether (DME) and methanol to maintain high utilization of the MTO feed to hydrocarbon products, recycle of the problematic oxygenates (ketones, aldehydes) leads to processing problems.

Therefore, there remains a need for an effective and efficient process for removing the unwanted or undesirable oxygenates from the recycle stream to an MTO reactor.

SUMMARY OF THE INVENTION

The present invention provides one or more processes for removing the unwanted or undesirable oxygenates from the recycle stream to an MTO reactor in an effective and efficient manner. Specifically, according to the present processes, methanol, which is one of the desired components in the recycle stream, is converted to DME. The conversion to DME allows for the desired oxygenates to be more easily separated from the oxygenates that are not as desired in the recycle stream. Specifically, DME is the most volatile of the oxygenate components of the recycle stream (boiling point of −24° C.) and is able to be easily separated from the other oxygenates via distillation. Acetaldehyde (boiling point of 20.2° C.) and acetone (boiling point of 56° C.) are more volatile than methanol (boiling point of 67.4° C.), requiring a separate distillation step to remove acetone and acetaldehyde from methanol. In addition, the heavier oxygenate byproducts (less volatile than methanol) also need to be removed from methanol to allow methanol and DME to be recycled, requiring yet another distillation step. However, by converting the methanol to DME, the separation between the desired and undesired oxygenates is done in an effective and efficient manner. In some processes of the present invention, the conversion and the separation are done in the same vessel; while in other processes of the present invention, the conversion and the separation are done in different vessels. Additionally, smaller oxygenates like acetone and acetaldehyde may be converted into heavier oxygenates that are more easily separated from the DME.

Accordingly, the present invention may be characterized, in at least one aspect, as providing a process for reducing heavy oxygenate recycle for an MTO reaction zone by: separating an effluent comprising light olefins, oxygenates, and water from an MTO reaction zone into a hydrocarbon product stream comprising light olefins and an aqueous stream comprising oxygenates and water; separating the aqueous stream into a water stream with reduced amount of oxygenates and an oxygenate-rich stream; increasing an amount of DME in the oxygenate-rich stream and separating the oxygenate-rich stream into a DME-rich stream and a heavy oxygenate-rich stream; and, recycling at least a portion of the DME-rich stream to the MTO reaction zone.

The present invention may also be characterized, in at least one aspect, as providing a process for reducing heavy oxygenate recycle for an MTO reaction zone by: passing a feed stream comprising methanol into an MTO reaction zone comprising a reactor operated under conditions to provide an effluent stream, the effluent stream comprising light olefins, oxygenates, and water; passing the effluent stream to a product separation zone configured to separate the effluent stream into a product stream comprising light olefins and an aqueous stream comprising oxygenates and water; passing the aqueous stream to an oxygenate stripping zone configured to provide an oxygenate-rich stream and a water stream with reduced amount of oxygenates; passing the oxygenate-rich stream to a conversion zone configured to convert methanol into DME, the conversion zone comprising a vessel and being configured to provide a DME-rich stream and a heavy oxygenate-rich stream; and, passing the DME-rich stream to the MTO reaction zone.

Furthermore, the present invention may also be generally characterized, in at least one aspect, in which the apparatus includes: an MTO reaction zone comprising a reactor operated under conditions to provide an effluent stream, the effluent stream comprising light olefins, oxygenates, and water; a product separation zone configured to separate the effluent stream into a product stream comprising light olefins and an aqueous stream comprising oxygenates and water; an oxygenate stripping zone configured to provide an oxygenate-rich stream and a water stream with reduced amount of oxygenates; and, a conversion zone configured to covert methanol into DME, the conversion zone comprising a vessel and being configured to provide a DME-rich stream and a heavy oxygenate-rich stream, wherein the DME-rich stream is recycled to the reaction zone.

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing figures, in which.

DETAILED DESCRIPTION OF THE INVENTION

As mentioned above, in the processes of the present invention, unreacted methanol from the effluent of the MTO reactor is converted to DME, and then primarily DME vapor is recycled to the MTO reactor. Additionally, acetone and acetaldehyde may be converted to heavy oxygenates which are more easily separated from the DME. Alternatively, a liquid product may be removed on the bottoms of the reactive distillation column that would contain the bulk of the acetone and acetaldehyde byproduct from MTO.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

As depicted, process flow lines in the figures can be referred to, interchangeably, as, e.g., lines, pipes, branches, distributors, streams, effluents, feeds, products, portions, catalysts, withdrawals, recycles, suctions, discharges, and caustics.

As used herein, the term "rich" can mean an increased amount of a compound or class of compounds in a stream relative to that in another stream.

As used herein, the term "depleted" can mean a decreased amount of a compound or class of compounds in a stream relative to that in another stream.

As used herein, the term "zone" can refer to an area including one or more equipment items and/or one or more sub-zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

With these general principles in mind, one or more embodiments of the present invention will be described with the understanding that the following description is not intended to be limiting.

Figure 1:
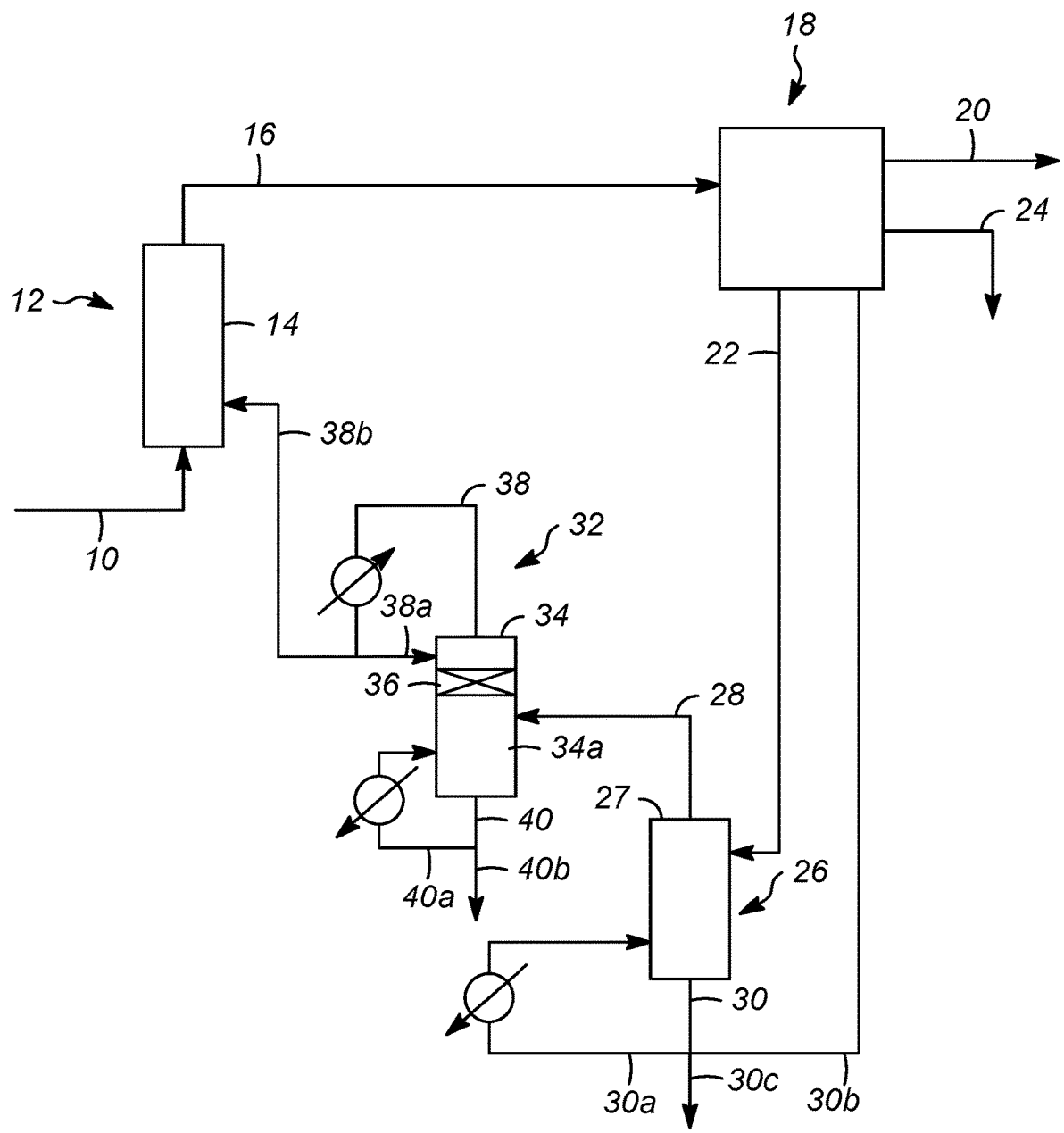
FIG. 1 shows a process flow diagram according to one or more embodiments of the present invention.
Figure 2:
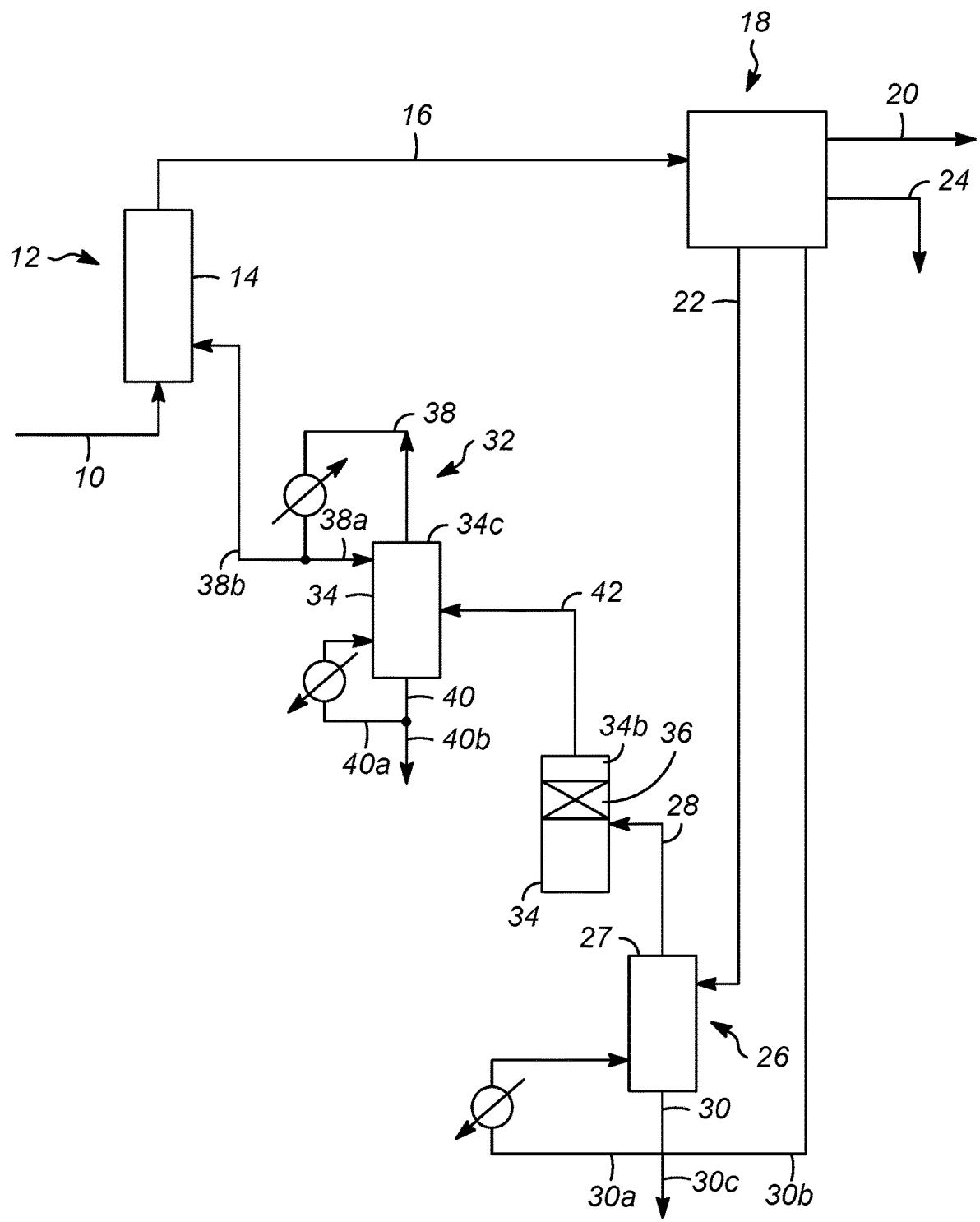
FIG. 2 shows another process flow diagram according to one or more embodiments of the present invention.

As shown in FIGS. 1 and 2, an oxygenate feed stream 10 is passed to an MTO reaction zone 12 having at least one reactor 14. The at least one reactor 14 of the MTO reaction zone 12 may be a fluidized bed reactor and includes an MTO catalyst that converts methanol and DME from the oxygenate feed stream 10 into olefins. Generally, the catalyst may be silicoaluminophosphate (SAPO), having a tetrahedral unit framework forming numerous pores to best contact methanol feed during conversion to olefins. Such MTO reactors and catalysts are known in the art, for example, in U.S. Pat. Nos. 6,166,282, 7,309,679, 7,423,191, and 9,643,897, the entireties of which are incorporated by reference herein.

An effluent from the effluent an MTO reaction zone 12 includes light olefins, oxygenates, and water. After separating catalyst from the effluent, an effluent stream 16 from the MTO reaction zone 12 may be passed to a product separation zone 18 configured to separate the effluent stream 16 into a product stream 20 comprising light olefins, as well as some other hydrocarbons, and an aqueous stream 22 comprising oxygenates and water. Additionally, the product separation zone 18 may provide a waste water stream 24. The product separation zone 18 is known in the art, for example, in U.S. Pat. No. 9,452,957, the entirety of which is incorporated by reference. The product stream 20, as is known, may be passed to a fractionation section (not shown) configured to separate the product stream 20 into different components streams.

The aqueous stream 22, comprising oxygenates and water, may be passed to an oxygenate stripping zone 26 having an oxygenate stripper 27 configured to provide an oxygenate-rich stream 28 and an oxygenate depleted water stream 30. A first portion 30a of the water stream 30 may be heated to partially vaporize the steam and subsequently returned to the oxygenate stripper 27. A second portion 30b of the water stream 30 may be passed back to the product separation zone 18. A third portion 30c of the water stream 30 may be sent for further processing.

Typically, the oxygenate-rich stream 28 would be recycled to the MTO reaction zone 12 to allow the methanol and DME therein to react. However, without more processing, the recycling of the oxygenate-rich stream 28 would lead to a buildup of heavy and/or undesired oxygenates in this stream. Accordingly, as indicated at the outset, according to the present processes the amount of DME is increased and then the DME is separated from the other oxygenates and recycled back to the MTO reaction zone 12. The oxygenate-rich stream 28 may be either a vapor or liquid, or a combination of both vapor and liquid, depending on the design and operation of oxygenate stripping zone 26.

As shown in FIGS. 1 and 2, the oxygenate-rich stream 28 is passed to a conversion zone 32 that includes one or more vessels 34. According to the embodiment shown in FIG. 1, the conversion zone includes one vessel 34 that is a reactive distillation column 34a. As is known, the reactive distillation column 34a includes one or more beds 36 of catalyst that, under the appropriate operation conditions, promotes a chemical reaction—in this case the conversion of methanol to DME. Such catalysts and operating conditions for the reactive distillation column 34a are known in the art. See, e.g., U.S. Pat. No. 5,817,906 and Azizi, et al. "Dimethyl ether: A review of technologies and productions challenges," Chemical Engineering and Processing, 2014, the entirety of which is incorporated by reference herein. Additionally, the catalyst may also promote the conversion of acetone and acetaldehyde to heavy oxygenates. In addition to the conversion of methanol to DME, the reactive distillation column 34a also separates the components within the reactive distillation column 34a into at least to component streams, namely, a DME-rich stream 38 and a heavy oxygenate-rich stream 40.

Turning to FIG. 2, in another embodiment of the present invention, the conversion zone 32 includes two vessels 34, the first of the two vessels 34 being a reactor 34b, or reaction vessel, which contains one or more of the beds 36 of catalyst. Again, the catalyst promotes the conversion of methanol to DME and may additionally promote the conversion of acetone and acetaldehyde to heavy oxygenates. The second of the two vessels 34 is a separation vessel 34c, such as a fractionation column, configured to separate an effluent stream 42 from the reactor 34b into the DME-rich stream 38 and the heavy oxygenate-rich stream 40. While the embodiment of FIG. 2, with a separate reactor 34b and separation vessel 34c, is believed to equally effective in reducing the amount of heavy oxygenates in the DME-rich stream 38, it is believed that the embodiment of FIG. 1 will provide for an increased conversion of the methanol to DME.

In either embodiment, a first portion 40a of the heavy oxygenate-rich stream 40 may be heated and then passed back to the reactive distillation column 34a or the separation vessel 34c. A second portion 40b of the heavy oxygenate-rich stream 40 may be passed to downstream processing.

Additionally, in both FIGS. 1 and 2, a first portion 38a of the DME-rich stream 38 is refluxed back to the reactive distillation column 34a or the separation vessel 34c, after being cooled. A second portion 38b of the DME-rich stream 38 is recycled back to the reactor 14 of the MTO reaction zone 12. As shown in FIGS. 1 and 2, the DME-rich stream 38 is cooled and then split into the two portions 38a, 38b. It is also contemplated that the DME-rich stream 38 is first split into the two portions 38a, 38b, and then only the first portion 38a (i.e., the refluxed portion) may be cooled. Thus, the DME-rich stream 38 may be recycled back to the reactor 14 of the MTO reaction zone 12 as either a liquid stream or a vapor stream.

The DME-rich stream 38 will also contain methanol, acetone, acetaldehyde, as well as some heavy oxygenates. The separation of the components may be done to allow some heavier oxygenates to slip into the DME-rich stream 38. However, the present processes provide a reduction of the amount of heavy oxygenates that is recycled to the MTO reaction zone 12.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

For example, the conditions of the conversion zone 32 may be adjusted as a result of a sensor that has determined that the amount of the heavy oxygenates in the MTO reaction zone 12 is below a threshold amount. Accordingly, the conversion zone 32 conditions may be adjusted to utilize less energy (and thus provide less of a conversion and a less stringent separation).

Thus, in the processes of the present invention, an efficient and effective reduction of the amount of heavy oxygenates in a recycle stream is provided for an MTO conversion process.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understanding the embodiments of the present invention.

Specific Embodiments

While the following is described in conjunction with specific embodiments, it will be understood that this description is intended to illustrate and not limit the scope of the preceding description and the appended claims.

A first embodiment of the invention is a process for reducing heavy oxygenate recycle for an MTO reaction zone, the process comprising separating an effluent comprising light olefins, oxygenates, and water from an MTO reaction zone into a hydrocarbon product stream comprising light olefins and an aqueous stream comprising oxygenates and water; separating the aqueous stream into a water stream with reduced amount of oxygenates and an oxygenate-rich stream; increasing an amount of DME in the oxygenate-rich stream and separating the oxygenate-rich stream into a DME-rich stream and a heavy oxygenate-rich stream; and, recycling at least a portion of the DME-rich stream to the MTO reaction zone. An embodiment of the invention is one, any or all of prior embodiments in this paragraph up through the first embodiment in this paragraph, wherein increasing the amount of DME in the oxygenate-rich stream comprises converting methanol to DME. An embodiment of the invention is one, any or all of prior embodiments in this paragraph up through the first embodiment in this paragraph, wherein methanol is converted into DME in a reactive distillation column. An embodiment of the invention is one, any or all of prior embodiments in this paragraph up through the first embodiment in this paragraph further comprising refluxing a portion of the DME-rich stream to the reactive distillation column. An embodiment of the invention is one, any or all of prior embodiments in this paragraph up through the first embodiment in this paragraph further comprising cooling the DME-rich stream before refluxing the portion of the DME-rich stream back to the reactive distillation column. An embodiment of the invention is one, any or all of prior embodiments in this paragraph up through the first embodiment in this paragraph, wherein methanol is converted into DME in a reaction vessel and wherein the oxygenate-rich stream is separated into the DME—rich stream and the heavy oxygenate-rich stream in a separation vessel, the separation vessel separate from the reaction vessel.

A second embodiment of the invention is a process for reducing heavy oxygenate recycle for an MTO reaction zone, the process comprising passing a feed stream comprising methanol into an MTO reaction zone comprising a reactor operated under conditions to provide an effluent stream, the effluent stream comprising light olefins, oxygenates, and water; passing the effluent stream to a product separation zone configured to separate the effluent stream into a product stream comprising light olefins and an aqueous stream comprising oxygenates and water; passing the aqueous stream to an oxygenate stripping zone configured to provide an oxygenate-rich stream and a water stream with reduced amount of oxygenates; passing the oxygenate-rich stream to a conversion zone configured to convert methanol into DME, the conversion zone comprising a vessel and being configured to provide a DME-rich stream and a heavy oxygenate-rich stream; and, passing the DME-rich stream to the MTO reaction zone. An embodiment of the invention is one, any or all of prior embodiments in this paragraph up through the second embodiment in this paragraph wherein the vessel of the conversion zone comprises a reactive distillation column. An embodiment of the invention is one, any or all of prior embodiments in this paragraph up through the second embodiment in this paragraph wherein the conversion zone comprises at least two vessels, the first vessel comprising a reactor and the second vessel comprising a separation vessel. An embodiment of the invention is one, any or all of prior embodiments in this paragraph up through the second embodiment in this paragraph further comprising passing the oxygenate-rich stream to the reactor in the conversion zone; and, passing an effluent stream from the reactor to the separation vessel. An embodiment of the invention is one, any or all of prior embodiments in this paragraph up through the second embodiment in this paragraph further comprising passing the water stream from the oxygenate stripping zone to the product separation zone. An embodiment of the invention is one, any or all of prior embodiments in this paragraph up through the second embodiment in this paragraph further comprising passing a portion of the DME-rich stream back to the conversion zone. An embodiment of the invention is one, any or all of prior embodiments in this paragraph up through the second embodiment in this paragraph further comprising cooling the DME-rich stream before passing the portion of the DME-rich stream back to the conversion zone. An embodiment of the invention is one, any or all of prior embodiments in this paragraph up through the second embodiment in this paragraph, further comprising at least one of sensing at least one parameter of the process and generating a signal or data from the sensing; generating and transmitting a signal; or generating and transmitting data.

A third embodiment of the invention is an apparatus for converting methanol to olefins, the apparatus comprising an MTO reaction zone comprising a reactor operated under conditions to provide an effluent stream, the effluent stream comprising light olefins, oxygenates, and water; a product separation zone configured to separate the effluent stream into a product stream comprising light olefins and an aqueous stream comprising oxygenates and water; an oxygenate stripping zone configured to provide an oxygenate-rich stream and a water stream with reduced amount of oxygenates; and, a conversion zone configured to covert methanol into DME, the conversion zone comprising a vessel and being configured to provide a DME-rich stream and a heavy oxygenate-rich stream, wherein the DME-rich stream is recycled to the reaction zone. An embodiment of the invention is one, any or all of prior embodiments in this paragraph up through the third embodiment in this paragraph wherein the conversion zone further comprises a second vessel, the second vessel comprising a separation vessel. An embodiment of the invention is one, any or all of prior embodiments in this paragraph up through the third embodiment in this paragraph wherein the vessel of the conversion zone comprises a reactive distillation column. An embodiment of the invention is one, any or all of prior embodiments in this paragraph up through the third embodiment in this paragraph wherein a portion of the DME-rich stream is cooled and then refluxed back to the reactive distillation column. An embodiment of the invention is one, any or all of prior embodiments in this paragraph up through the third embodiment in this paragraph wherein a portion of the DME-rich stream is cooled and then passed back to the conversion zone. An embodiment of the invention is one, any or all of prior embodiments in this paragraph up through the third embodiment in this paragraph wherein the water stream is recycled to the product separation zone.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for reducing heavy oxygenate recycle for an MTO reaction zone, the process comprising:

separating an effluent comprising light olefins, oxygenates, and water from an MTO reaction zone into a hydrocarbon product stream comprising light olefins and an aqueous stream comprising oxygenates and water; separating the aqueous stream into a water stream with reduced amount of oxygenates and an oxygenate-rich stream;

increasing an amount of DME in the oxygenate-rich stream and separating the oxygenate-rich stream into a DME-rich stream and a heavy oxygenate-rich stream; and, recycling at least a portion of the DME-rich stream to the MTO reaction zone.

2. The process of claim 1, wherein the oxygenates comprise unreacted methanol and the increasing the amount of DME in the oxygenate-rich stream comprises converting the methanol to DME.

3. The process of claim 2, wherein the methanol is converted into DME in a reactive distillation column.

4. The process of claim 3 further comprising:
refluxing a portion of the DME-rich stream to the reactive distillation column.

5. The process of claim 4 further comprising:
cooling the DME-rich stream before refluxing the portion of the DME-rich stream back to the reactive distillation column.

6. The process of claim 2, wherein the methanol is converted into DME in a reaction vessel and wherein the oxygenate-rich stream is separated into the DME-rich stream and the heavy oxygenate-rich stream in a separation vessel, the separation vessel separate from the reaction vessel.

7. A process for reducing heavy oxygenate recycle for an MTO reaction zone, the process comprising:
passing a feed stream comprising methanol into an MTO reaction zone comprising a reactor operated under conditions to provide an effluent stream, the effluent stream comprising light olefins, oxygenates, and water, wherein the oxygenates comprise unreacted methanol;
passing the effluent stream to a product separation zone configured to separate the effluent stream into a product stream comprising light olefins and an aqueous stream comprising oxygenates and water;
passing the aqueous stream to an oxygenate stripping zone configured to provide an oxygenate-rich stream and a water stream with reduced amount of oxygenates;
passing the oxygenate-rich stream to a conversion zone configured to convert the methanol into DME, the conversion zone comprising a vessel and being configured to provide a DME-rich stream and a heavy oxygenate-rich stream; and,
passing the DME-rich stream to the MTO reaction zone.

8. The process of claim 7 wherein the vessel of the conversion zone comprises a reactive distillation column.

9. The process of claim 7 wherein the conversion zone comprises at least two vessels, the first vessel comprising a reactor and the second vessel comprising a separation vessel.

10. The process of claim 9 further comprising:
passing the oxygenate-rich stream to the reactor in the conversion zone; and,
passing an effluent stream from the reactor to the separation vessel.

11. The process of claim 7 further comprising:
passing the water stream from the oxygenate stripping zone to the product separation zone.

12. The process of claim 7 further comprising:
passing a portion of the DME-rich stream back to the conversion zone.

13. The process of claim 12 further comprising:
cooling the DME-rich stream before passing the portion of the DME-rich stream back to the conversion zone.

14. The process of claim 7, further comprising at least one of:
sensing at least one parameter of the process and generating a signal or data from the sensing;
generating and transmitting a signal; or
generating and transmitting data.

15. An apparatus for converting methanol to olefins, the apparatus comprising:
an MTO reaction zone comprising a reactor operated under conditions to provide an effluent stream, the effluent stream comprising light olefins, oxygenates, and water;
a product separation zone configured to separate the effluent stream into a product stream comprising light olefins and an aqueous stream comprising oxygenates and water;
an oxygenate stripping zone configured to provide an oxygenate-rich stream and a water stream with reduced amount of oxygenates; and,
a conversion zone configured to covert methanol into DME, the conversion zone comprising a vessel and being configured to provide a DME-rich stream and a heavy oxygenate-rich stream, wherein the DME-rich stream is recycled to the reaction zone.

16. The apparatus of claim 15 wherein the conversion zone further comprises a second vessel, the second vessel comprising a separation vessel.

17. The apparatus of claim 15 wherein the vessel of the conversion zone comprises a reactive distillation column.

18. The apparatus of claim 17 wherein a portion of the DME-rich stream is cooled and then refluxed back to the reactive distillation column.

19. The apparatus of claim 15 wherein a portion of the DME-rich stream is cooled and then passed back to the conversion zone.

20. The apparatus of claim 19 wherein the water stream is recycled to the product separation zone.

* * * * *